(12) United States Patent
Chen et al.

(10) Patent No.: US 7,795,234 B2
(45) Date of Patent: Sep. 14, 2010

(54) NEWLY IDENTIFIED HUMAN SMALL INTESTINE EXTRACELLULAR LACTASE-PHLORIZIN HYDROLASE (ECLPH) GENE

(75) Inventors: Chuan-Mu Chen, Taichung (TW); Winston T. K. Cheng, Taipei (TW); Hsiao-Ling Chen, Taipei (TW)

(73) Assignee: National Chung Hsing University, Taichung (TW)

( * ) Notice: Subject to any disclaimer, the term of this patent is extended or adjusted under 35 U.S.C. 154(b) by 274 days.

(21) Appl. No.: 11/901,989

(22) Filed: Sep. 20, 2007

(65) Prior Publication Data

US 2008/0090279 A1    Apr. 17, 2008

Related U.S. Application Data

(62) Division of application No. 11/434,332, filed on May 15, 2006, now Pat. No. 7,501,554.

(51) Int. Cl.
*A01N 43/04* (2006.01)
*C07H 21/04* (2006.01)
*C12N 15/00* (2006.01)

(52) U.S. Cl. .................. 514/44 R; 536/23.2; 435/320.1

(58) Field of Classification Search .................. 514/44; 536/23.2; 435/320.1
See application file for complete search history.

(56) References Cited

U.S. PATENT DOCUMENTS 5,907,080 A * 5/1999 Karatzas et al. ............... 800/25

OTHER PUBLICATIONS

Mantei et al. EMBO J. 7:2705-2713; 1988.*
Berns, K.I., et al., "Adeno-Associated Viruses," Advances in Virus Research, vol. 25, p. 407, 1979.
Bowie, et al.: "Deciphering the Message in Protein Sequences: Tolerance to Amino Acid Substitutions," Science, vol. 244, pp. 1306-1310, 1990.
During, M., et al., "Peroral gene therapy of lactose intolerance using an adeno-associated virus vector," Nature Medicine, vol. 4, No. 10, pp. 1131-1135, Oct. 1998.
L'Huillier, P., et al., "Efficient and specific ribozyme-mediated reduction of bovine α-lactalbumin expression in double transgenic mice," Proc. Natl. Acad. Sci. USA, vol. 93, vol. 6698-6703, Jun. 1996.
Skolnick, J., et al., "From genes to protein structure and function: novel applications of computational approaches in the genomic era," Tibtech, vol. 18, pp. 34-39, 2000.
Stinnakre, M.G., et al., "Creation and phenotypic analysis of α-lactalbumin-deficient mice," Proc. Natl. Acad. Sci. USA, vol. 91, pp. 6544-6548, Jul. 1994.

* cited by examiner

*Primary Examiner*—Fereydoun G Sajjadi
(74) *Attorney, Agent, or Firm*—Panitch Schwarze Belisario & Nadel LLP

(57) ABSTRACT

The invention provides a transgenic animal producing low-lactose milk, which is transformed with a gene encoding an extracellular lactase-hydrolyzing enzyme cloned from a human small intestinal cDNA library. The invention also provides a new extracellular lactase-phlorizin hydrolase (ecLPH) gene that can express human lactase-hydrolyzing enzyme in the mammary gland of animals. The invention can be used in the production of low-lactose milk.

6 Claims, 3 Drawing Sheets
(2 of 3 Drawing Sheet(s) Filed in Color)

Fig 4
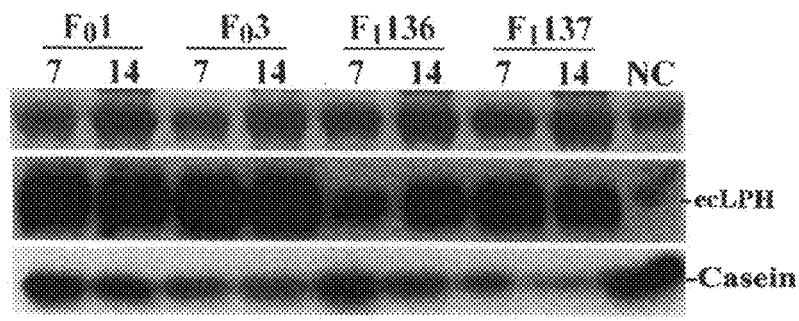
Fig 5A
Fig 5B
Fig 5C
(A) Heterozygote mouse (ecLPH +/-)
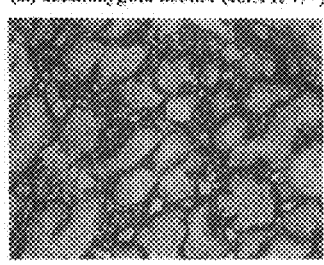
(B) Homozygote mouse (ecLPH +/+)
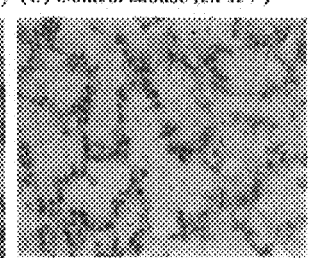
(C) Control mouse (LPH-/-)
Fig 6A
Fig 6B
Fig 6C
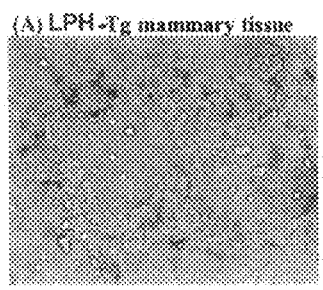
(A) LPH-Tg mammary tissue
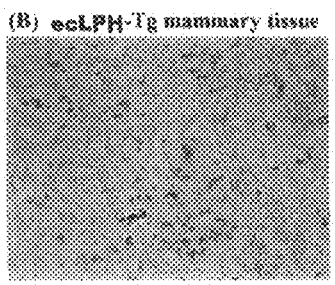
(B) ecLPH-Tg mammary tissue
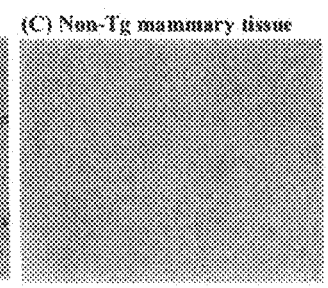
(C) Non-Tg mammary tissue

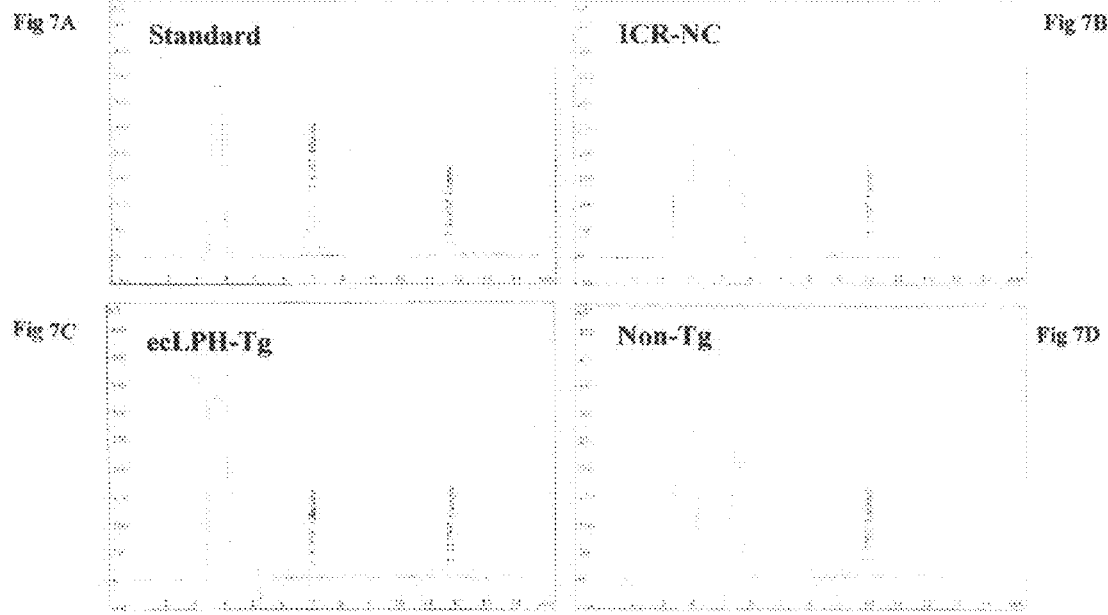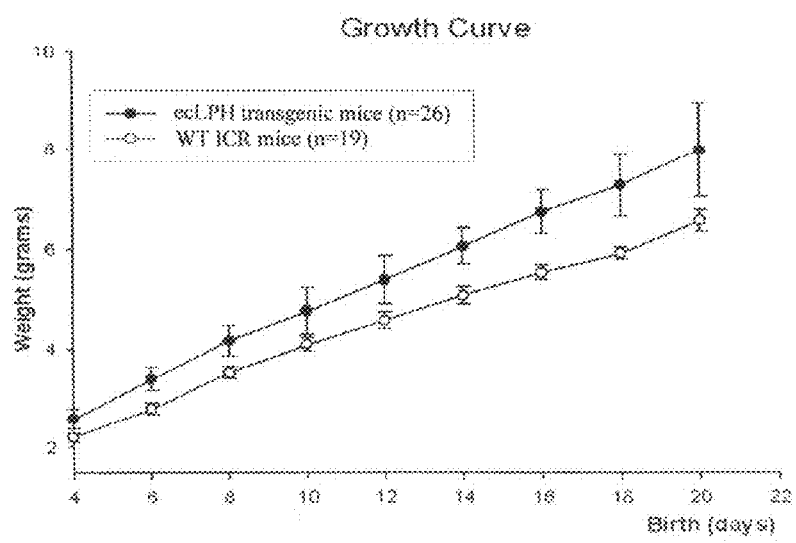

NEWLY IDENTIFIED HUMAN SMALL INTESTINE EXTRACELLULAR LACTASE-PHLORIZIN HYDROLASE (ECLPH) GENE

CROSS-REFERENCE TO RELATED APPLICATIONS

This application is a divisional application of U.S. patent application Ser. No. 11/434,332, filed May 15, 2006, the contents of which are hereby incorporated herein by reference.

FIELD OF THE INVENTION

The present invention relates to the biotechnical field of gene cloning and transgenic animals, which utilizes a genetic cloning technique involving the human genomic library, and development of mammary gland-specific expression vectors to provide a platform technology of transgenic animals producing low-lactose milk. More specifically, the present invention also provides a new extracellular lactase-phlorizin hydrolase (ecLPH) gene, which can be used to transform animals to produce low-lactose milk.

BACKGROUND OF THE INVENTION

Milk is a food source of high nutrition value, which is rich in proteins, vitamins, carbohydrates, calcium and other minerals. Except for being utilized as the nutrition source for newborn babies and infants, it can also be used to prevent osteoporosis in older people, and especially elderly people. Lactose is the major carbohydrate in milk. However, people with lactose intolerance cannot decompose the abundant lactose in milk, which is caused by reduction in the activity of lactase-phlorizin hydrolase. Un-decomposed lactose accumulates in the intestine and induces bacterial fermentation, producing carbon dioxide, hydrogen and methane and resulting in symptoms such as abdominal distension, nausea and diarrhea. Such disadvantages limit the use of milk and dairy products including milk or lactose.

The best strategy to treat patients suffering from lactose intolerance syndrome or to prevent the syndrome, is to avoid the ingestion of dairy products containing large amounts of lactose. However, many people, including lactose-intolerant people, enjoy dairy products containing milk or otherwise containing lactose. Therefore, the development of low-lactose milk and other dairy products containing lactose is crucial. It is now known that α-lactalbumin is an abundant calcium metalloprotein in milk. The binding between α-lactalbumin and galactosyltransferase in the Golgi body can modify the specificity of the galactosyltransferase by forming the lactose synthetase binary complex to synthesize lactose. In order to understand the effect of α-lactalbumin on lactogenesis and the relationship between α-lactalbumin and lactose, Stinnakre et al. utilized gene targeting in embryonic stem cells to produce transgenic mice with heterozygous or homozygous deficiencies in the α-lactalbumin gene. They found that the milk of the transgenic mice with homozygous deficiencies in the α-lactalbumin gene lacked not only α-lactalbumin but also lactose. However, the lack of lactose resulted in highly viscous milk since lactose is an important regulator of osmotic pressure during lactation, and thus the female mice cannot feed their pups smoothly. In the milk of the transgenic mice with heterozygous deficiencies in the α-lactalbumin gene, α-lactalbumin decreased by 40% while lactose decreased by 10-20% (Stinnakre, M. G., Vilotte, J. L., Soulier, S. and Mercier, J. C., 1994. Creation and phenotype analysis of α-lactalbumin-deficient mice. Proc. Natl. Acad. Sci. 91: 6544-6548).

In 1996, L'Huillier et al. created a construct wherein a ribozyme 5 (RZ5) gene is downstream of the mouse mammary tumor virus (MMTV) long terminal repeat (LTR) so that the RZ5 gene can be specifically expressed in mammary gland cells. Utilizing gene-transformation technology, transgenic mice highly expressing the RZ5 gene in their mammary glands were developed. RZ5 can specifically degrade α-lactalbumin mRNA to reduce the production of α-lactalbumin and further affects the production of lactose (L'Huillier, P. J., Soulier, S., Stinnakre, M. G., Lepourry, L., Davis, S. R., Mercier, J. C. and Vilotte, J. L., 1996. Efficient and specific ribozyme-mediated reduction of bovine alpha-lactalbumin expression in double transgenic mice. Proc. Natl. Acad. Sci. 93: 6698-6703). According to the studies of Berns and Hauswirth (1979), adeno-associated virus (AAV), which is tissue-specific, uses cells in the tissues of human respiratory and gastrointestinal systems as host cells. Moreover, since AAV is resistant to high temperature and low pH, it is potentially resistant to oral administration (Bern, K. I. and Hauswirth, W. W., 1979. Adeno-associated viruses. Adv. Virus. Res. 25: 407-409). In 1998, During et al. reconstructed AAV into a vector, wherein most of the AAV genes were deleted and only 145 bp of terminal repeats were retained. The resulting AAV vector contains few viral genes so that the possibilities of gene recombination and viral gene expression were reduced to minimum. Then a β-galactosidase gene was constructed onto the AAV vector, and the vector was fed to rats through oral administration. It is found that the β-galactosidase gene was highly expressed at the 6th hour post feeding, and the expression was sustained and stable through 6 months (During, M. J., Xu, R., Young, D., Kaplitt, M. G., Sherwin, R. S. and Leone, P., 1998. Peroral gene therapy of lactose intolerance using an adeno-associated virus vector. Nature Medicine 4: 1131-1135).

Even in view of the aforementioned studies, acceptable low-lactose milk has not been developed. In one aspect, the normal osmotic pressure of lactation is affected. In another aspect, the use of viral vectors has potential danger. Therefore, the development of a new technique for producing low-lactose milk and other dairy products containing lactose is necessary. The present invention satisfies this necessity.

BRIEF SUMMARY OF THE INVENTION

One aspect of the present invention relates to a transgenic animal producing low-lactose milk, which is transformed with a gene encoding an extracellular lactase-hydrolyzing enzyme, wherein the gene is cloned from a human small intestinal cDNA library. Preferably, the gene is a gene encoding an extracellular lactase-phlorizin hydrolase (ecLPH).

Another aspect of the present invention relates to an isolated new extracellular lactase-phlorizin hydrolase gene cloned from a human small intestinal cDNA library that can be expressed with a mammary gland-specific expression vector.

A further aspect of the present invention relates to a heterologous gene expression vector construct, comprising the extracellular lactase-phlorizin hydrolase (ecLPH) gene of the present invention constructed in a mammary gland-specific expression vector which can be expressed in a mammary gland.

Yet another aspect of the present invention relates to an isolated extracellular lactase-phlorizin hydrolase gene cloned from a human small intestinal cDNA library that can be expressed with a mammary gland-specific expression vector, encoding an extracellular protein without a membrane-binding domain, the gene lacking Exon 12 and Exon 15-17 compared with a known human lactase-phlorizin hydrolase (hLPH) gene.

A still further aspect of the present invention relates to a method for producing low-lactose milk, wherein the heterologous gene expression vector construct of the present invention is introduced into a pronucleus to produce a transgenic animal, which produces low-lactose milk to benefit the large group of people suffering from lactose intolerance syndrome.

Another aspect of the present invention relates to a heterologous gene expression vector construct comprising the gene of the present invention that can be expressed with a mammary gland-specific expression vector, and (1) a promoter 5'-regulatory sequence, which is specific for expression in mammary gland epithelial cells and can regulate the heterologous gene so that the gene is continuously and stably expressed during a lactation period of a transgenic mammal; (2) a mammary gland-specific extracellular signal peptide sequence, which can guide the heterologous proteins expressed in the mammary gland epithelial cells of the transgenic mammal so that the proteins are efficiently secreted into milk produced by the transgenic mammal; (3) a heterologous gene, which is downstream of and regulated by the 5'-regulatory sequence and the extracellular signal peptide sequence; and (4) a 3'-regulatory sequence, which is downstream of the coding sequence of the heterologous gene, comprising a polyadenylation signal sequence for stability and integrity of an mRNA molecule transcribed from the heterologous gene and post-transcriptional modification.

A further aspect of the present invention relates to a method for producing low-lactose milk, comprising providing the transgenic animal of the present invention, and obtaining the low-lactose milk from the transgenic animal.

Another aspect of the present invention relates to a method for increasing the growth rate and weight gain of a newborn animal, comprising providing a maternal milk-producing animal and transforming the animal by introducing into the animal the extracellular lactase-phlorizin hydrolase gene of the present invention, and feeding the newborn animal with milk secreted by the maternal animal after pregnancy and delivery of the newborn animal.

Still another aspect of the present invention relates to a method for producing a transgenic animal that produces low-lactose milk, comprising providing a milk-producing animal and transforming the animal by introducing into the animal a gene encoding an extracellular lactase-hydrolyzing enzyme cloned from a human small intestinal cDNA library.

As used herein, the singular forms "a", "an", and "the" include plural referents unless the context clearly indicates otherwise.

BRIEF DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1A shows colonies of the cDNA phage clones obtained after three rounds of screening. FIG. 1B is the restriction digestion map of the ecLPH phage clones.

FIG. 3A is a map of the transgene construct. FIG. 3B and FIG. 3C show the results of Southern blot analysis of the transgenic mouse genomes of different lines in transgenic founder ($F_0$) and their offsprings ($F_1$) (transgenic line #3 is shown in FIG. 3B and transgenic line #5 is shown in FIG. 3C), which prove that the heterologous ecLPH gene has indeed been inserted into the chromosomes of transgenic animals. FIG. 3D shows the result of express PCR analysis of the transgenic mice (M1-M7) and transgenic goats (G1-G3).

FIG. 4 shows the result of Western blot analysis of the ecLPH proteins secreted in the milk of the transgenic animals of the present invention. Milk of transgenic mice and normal mice was diluted 20-fold and centrifuged to remove milk lipid. SDS-PAGE and Western blot analysis were performed.

FIGS. 5A-5C show immuno-histochemistry staining of mammary gland tissue sections of the ecLPH transgenic mice of the present invention. Immuno-histochemistry staining was performed to the mammary gland tissues of transgenic mice (FIGS. 5A and 5B) and normal mice (FIG. 5C) with monoclonal antibodies specific for LPH protein. Mammary-gland tissues were taken on the $14^{th}$ day of the lactation period. Antibody staining analysis showed that homozygous transgenic female mice (FIG. 5B) expressed more ecLPH proteins than heterozygous ones (FIG. 5A).

FIGS. 6A-6C show X-Fuc activity staining of the mammary-gland freeze sections of transgenic mice and normal mice during the lactation period. Transgenic female mice and normal female mice were sacrificed on the $14^{th}$ day of their lactation period, and their mammary-gland tissues were taken for sectioning. Activity staining was performed on the mammary-gland sections of the transgenic mice (FIG. 6A and FIG. 6B) and normal mice (FIG. 6C) with the X-Fuc chromogen. The results showed that both LPH and ecLPH of the transgenic mice were active. Also, the ecLPH appearing in the activity-stained sections of FIG. 6B proved its extracellular property.

FIGS. 7A-7D show the results obtained by examining the lactose-degrading ability of the human ecLPH enzyme, which was expressed from the mammary gland-specific expression vector of the present invention and secreted into the milk of the transgenic animals during lactation. FIG. 7A shows standard samples of glucose, the monosaccharide molecule, and lactose, the disaccharide molecule, established by HPLC. FIG. 7B shows an HPLC separation curve of lactose in the milk sample from a normal ICR mouse, used as the normal control of the experiment in Example 6. FIG. 7C shows an HPLC map of the milk sample from an ecLPH transgenic mouse, showing that 50% of the lactose was degraded to glucose. FIG. 7D shows an HPLC map of the milk sample from a non-transgenic mouse, proving that the milk contained only lactose.

FIG. 8 shows a comparison of the youngling growth curves of ecLPH transgenic mice and normal ICR mice in the lactation period. In each brood of the normal ICR mice and transgenic mice, the subject numbers of the younglings were controlled between 8 to 10. The weights of the younglings of the normal ICR mice and transgenic mice were measured every two days from the $4^{th}$ day after birth. Statistical data showed that the two groups had a significant difference of $p<0.001$ during the $4^{th}$ to $20^{th}$ days after birth.

DETAILED DESCRIPTION OF THE INVENTION

The present invention provides a transgenic animal producing low-lactose milk, wherein the transgenic animal is transformed with a novel gene encoding an extracellular lactase-hydrolyzing enzyme cloned from a human small intestinal cDNA library according to the present invention. According to an embodiment of the present invention, the gene encoding an extracellular human lactase-hydrolyzing enzyme of the present invention is preferably an extracellular human lactase-phlorizin hydrolase gene, more preferably the new extracellular human lactase-phlorizin hydrolase gene of the present invention (ecLPH). The newly identified ecLPH cDNA clone containing a secreting signal peptide in the N-terminus and lacking a transmembrane domain in the C-terminus was verified as encoding a membrane-anchorless extracellular protein in this invention when compared to the known human lactase-phlorizin hydrolase (hLPH) gene. Since the extracellular lactase-hydrolyzing enzyme gene is constructed in a mammary gland-specific expression vector, after being introduced into an animal, the transgene can be continuously and stably expressed during lactation, producing large amounts of proteins with the activity of degrading lactose. The expression of the heterologous gene in tissues of the mammary gland does not affect the normal physiological functions of the transgenic animal. The transgene specific for mammary gland expression even lacks any additional selection gene for antibiotic resistance. Further, mammals transformed by the technology of the present invention breed filial generations carrying the heterologous transgene, with amounts of expression comparable to their transformed parental generation and thus can be used to produce low-lactose milk.

The present invention also provides a method for producing a transgenic animal that produces low-lactose milk, wherein the animal is transformed with a gene encoding an extracellular lactase-hydrolyzing enzyme, preferably an extracellular lactase-phlorizin hydrolase gene, more preferably the extracellular lactase-phlorizin hydrolase gene of the present invention (ecLPH). The newly identified ecLPH cDNA clone containing a secreting signal peptide in the N-terminus and lacking a transmembrane domain in the C-terminus was proposed as a membrane-anchorless extracellular protein in this invention when compared to the known human lactase-phlorizin hydrolase (hLPH) gene. The inventors have clearly demonstrated that the exogenous ecLPH protein can be secreted into the mammary alveolar cavity (FIG. 6B) of lactating transgenic mice. In contrast, the exogenous hLPH protein can only be found in the membrane portion of the mammary gland (FIG. 6A) of lactating transgenic mice.

According to an example of the present invention, the animal was transformed with the heterologous gene expression vector construct of the present invention.

Figure 2A:
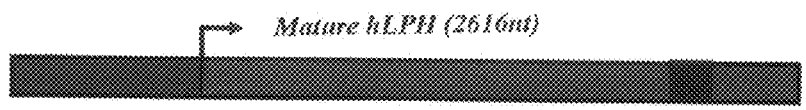
FIGS. 2A and 2B show the cDNA structure of the newly cloned extracellular lactase-phlorizin hydrolase (ecLPH) gene of the present invention (FIG. 2B) compared to the known human lactase-phlorizin hydrolase (hLPH) gene (FIG. 2A). The hLPH-encoded protein containing a secretion signal peptide in the N-terminus (initial red box region in the FIG. 2A) and a transmembrane domain (green box region in FIG. 2A) has been reported as a membrane-anchored protein in the intestinal epithelia. However, the newly identified human ecLPH cDNA structure contains an alternative splicing in the transmembrane domain of hLPH and a novel 3'-UTR sequence (yellow box region in FIG. 2B). This clone was examined as a feature of the membrane-anchorless extracellular protein in the present invention.
Figure 2B:
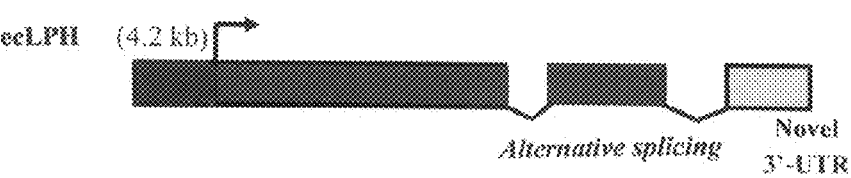

Another embodiment of the present invention also provides a novel extracellular human lactase-phlorizin hydrolase (ecLPH) gene, which was cloned from a human small intestinal cDNA library and can be expressed with a mammary gland-specific expression vector. The ecLPH cDNA of the present invention has a full length of 4.2 kb, and encodes an extracellular protein without a membrane-binding domain. Compared with the gene sequence of the known mature human lactase-phlorizin hydrolase (hLPH) (FIG. 2A), the ecLPH cDNA of the present invention (FIG. 2B) lacks Exon 12 and Exon 15-17, which completely spliced out the transmembrane domain. The coding region structure of the ecLPH cDNA of the present invention is shown in FIGS. 2A and 2B. The newly identified ecLPH cDNA clone containing a secreting signal peptide in the N-terminus and lacking a transmembrane domain in the C-terminus was verified as a membrane-anchorless extracellular protein in this invention.

According to an embodiment of the present invention, the extracellular human lactase-phlorizin hydrolase gene of the present invention has a nucleotide sequence encoding the amino acid sequence as shown in SEQ ID NO: 2.

According to a preferred embodiment of the present invention, the extracellular human lactase-phlorizin hydrolase gene of the present invention has the nucleotide sequence as shown in SEQ ID NO: 1, or a degenerate sequence or a complementary sequence thereof.

Figure 3A:
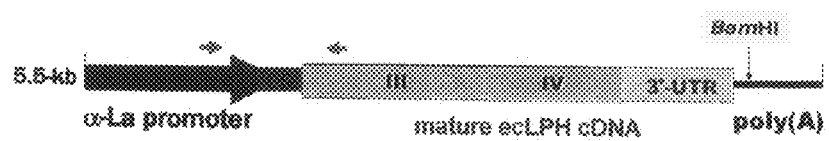
FIGS. 3A-3D show the results obtained by examining the ecLPH genes in the genomes of the transgenic mice and dairy goats of the present invention.

In another embodiment, the present invention relates to a heterologous gene expression vector construct comprising the gene of the present invention that can be expressed with a mammary gland-specific expression vector. More specifically, the construct comprises four parts: (1) a promoter 5'-regulatory sequence, which is specific for expression in the mammary gland epithelial cells and can regulate the heterologous gene so that the gene is continuously and stably expressed during the lactation period of the transgenic mammal; (2) a mammary gland-specific extracellular signal peptide sequence, which can guide the heterologous proteins expressed in the mammary gland epithelial cells of the transgenic mammal so that the proteins are efficiently secreted into the milk; (3) a heterologous gene, which is downstream of and regulated by the 5'-regulatory sequence and the extracellular signal peptide; and (4) a 3'-regulatory sequence, which is downstream of the coding sequence of the heterologous gene, comprising a polyadenylation signal sequence for the stability and integrity of the mRNA molecule transcribed from the heterologous gene and post-transcriptional modification. According to an embodiment of the present invention, the novel extracellular lactase-phlorizin hydrolase (ecLPH) gene of the present invention is constructed downstream of the mammary-gland specific promoter, followed by the polyadenylation signal sequence (0.5 kb) of a bovine growth factor gene to form a mammary gland-specific mammalian vector. The map of the transgene construct is shown in FIG. 3A.

A further embodiment of the present invention relates to a method for producing low-lactose milk, wherein the heterologous gene expression vector construct of the present invention is introduced into a pronucleus to produce a transgenic animal that produces low-lactose milk. According to an example of the present invention, the milk of the transgenic animal showed that the heterologous gene was highly expressed in the mammary gland, and the transgene was continuously and stably expressed during lactation to produce large amounts of proteins with the activity of degrading lactose. This proved that the transgenic animal could indeed be used to produce low-lactose milk.

In addition, it was surprisingly found in the present invention that when transgenic female mice of the present invention mated during the same period with normal ICR female mice and fed their pups with the milk secreted after their pregnancy and delivery, the weights of pups receiving milk from the LPH transgenic mice increased more than those of the normal ICR control group, with a statistically significant difference (p<0.001) (shown in FIG. 8). This result not only showed that the novel ecLPH protein had a function of degrading lactose, but also indicated that the transformed monosaccharide components (i.e., glucose and galactose) could be digested more easily and might provide assistance in intestinal digestion and absorption. The result also indicated that the ability to lactate was raised due to a change of the role of lactose in balancing the osmotic pressure. Accordingly, the present invention also provides a method for increasing the growth rate and weight gain of a newborn animal, comprising transforming a maternal animal with the extracellular lactase-phlorizin hydrolase gene of the present invention, and feeding the newborn animal with the milk secreted after pregnancy and delivery of the transformed animal, preferably from the pregnant transgenic animal.

The aforementioned animals refer to mammals, including but not limited to mice, cows, goats and sheep, preferably cows, goats and sheep.

The following examples are provided for further illustrating the present invention, but not for limiting the present invention.

EXAMPLE 1

Screening for a Novel Extracellular Lactase-Phlorizin Hydrolase (ecLPH) Gene in a Human Small Intestine 5'-Stretch cDNA Library The screening was conducted with small fragments of specific LPH nucleotides in a human small intestine 5'-stretch cDNA library. The small fragments of specific human LPH nucleotides were obtained from the GenBank of NCBI Sequence Viewer (Accession Number: X07994) for the designation of primer sets to generate a probe used in cDNA library screening. The primers used in screening for LPH cDNA are:

```
Primer 1:
                             (SEQ ID NO: 3)
5'-CTCTCTTGTCATCCTCTTCC-3';
and Primer 2:
                             (SEQ ID NO: 4)
5'-AACAAGTCAATCAAGGCAGG-3'.
```

The primers used in screening for ecLPH cDNA are:

```
Primer 3:
                             (SEQ ID NO: 5)
5'-CAGACTTTTGTTTCCAGACC-3';

Primer 4:
                             (SEQ ID NO: 6)
5'-TCAACAACACGAACAGGC-3';
```

```
and

Primer 5:
                             (SEQ ID NO: 7)
5'-ACAGAAATGCCAAGCCACAG-3'.
```

Figure 1A:
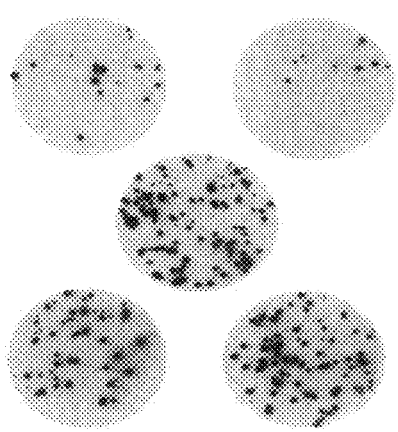
FIGS. 1A and 1B show the results obtained by screening the human small intestine 5'-stretch cDNA library for the newly cloned extracellular lactase-phlorizin hydrolase (ecLPH) gene of the present invention.
Figure 1B:
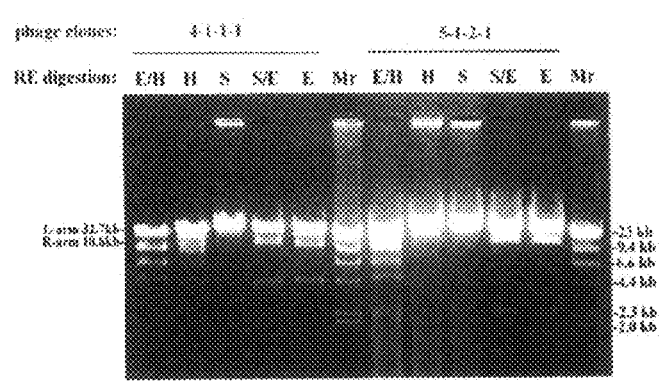

In the first round, a total of $5 \times 10^4$ pfu phages were screened. Developed X-ray films were properly cut and oriented with the phage culture plates to check for hybridization signals on the X-ray films. Only those culture plates with overlapping hybridization signals on the X-ray films developed from two duplicate nitrocellulose (NC) films were selected. A total of five hybridization signal spots were screened out in the first round, designated as 1-1, 4-1, 4-2, 4-3 and 5-1, respectively. The concentrations of the phages were determined by a rapid quantitative method using a serial dilution of phage plating on agar plates, followed by the second and third rounds of screening. The concentrations of the five recombinant phage clones obtained after three rounds of screening were determined by the same rapid quantitative method. The phages were proliferated in 150 mm culture plates to obtain a high-concentration phage liquid. Phage DNA was extracted by phenol/chloroform purification and ethanol precipitation, and the insert fragment was analyzed by restriction digestion (shown in FIG. 1B).

The DNA of the five recombinant phage strains was digested with EcoRI to separate the vector from the carried hLPH cDNA fragment, and then analyzed by 0.8% gel electrophoresis. It was found that three of the clones carried the same hLPH cDNA fragment, which was about 6.2 kb, while the other two clones carried a cloned fragment of about 4.2 kb. The two types of clones were designated as 4-1-1-1 and 5-1-2-1, respectively, and were fully sequenced. The results of the sequencing showed that the cloned 6.2 kb hLPH fragment (No. 4-1-1-1) encoded a membrane-anchored protein comprising a membrane-binding domain, while the cloned 4.2 kb ecLPH fragment (No. 5-1-2-1) encoded an extracellular protein comprising no membrane-binding domain, which is the novel ecLPH of the present invention. The gene coding region structure of the novel ecLPH cDNA is shown in FIG. 2. The various colored sections in FIG. 2 of LPH and ecLPH (also called LPH1) mRNA structures are indicated, where present, as a precursor sequence (blue box region), a mature lactase-phlorizin hydrolase domain (red box region), a transmembrane domain (green box region), and a novel 3'-UTR region (yellow box region). The known hLPH cDNA has a full length of 6.2 kb and encodes a membrane-anchored protein comprising a membrane-binding domain, while the newly cloned ecLPH (also called LPH1) cDNA has a full length of 4.2 kb and lacks Exon 12 and Exon 15-17, encoding an extracellular protein comprising no membrane-binding domain.

After sequencing, the genetic sequence was deduced for the ecLPH gene and expressed protein of the present invention. The nucleotide sequence is SEQ ID NO: 1 and the amino acid sequence is SEQ ID NO: 2.

EXAMPLE 2

Figure 3B:
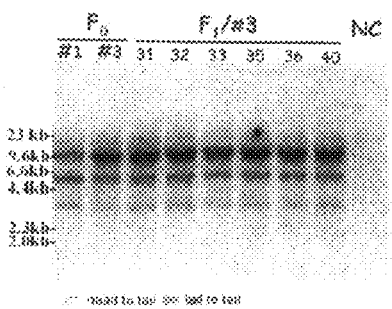
Figure 3C:
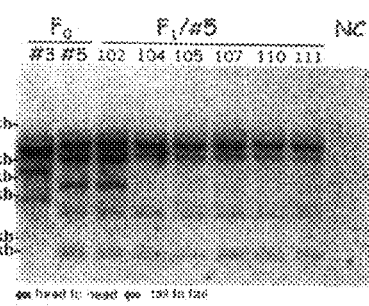
Figure 3D:
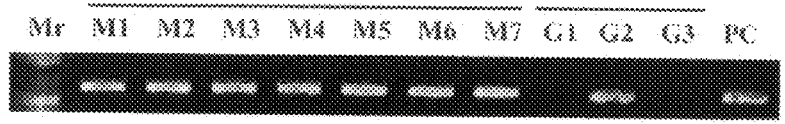

Production of Transgenic Mice and Dairy Goats Carrying the Lactase-Phlorizin Hydrolase (ecLPH) Gene According to the present invention, to breed a transgenic mammal, the extracellular human lactase-phlorizin hydrolase (ecLPH) gene was constructed into a mammary gland-specific alpha-lactalbumin (α-LA) promoter (2.0 kb) by DNA ligation reaction, followed by the polyadenylation signal sequence (0.5 kb) of a bovine growth factor gene (bGH polyA) to form a mammary gland-specific mammal vector. A map of the transgene construct is shown in FIG. 3A. The various colored sections in FIG. 3A of the transgene map indicated a mammary gland-specific α-LA promoter (dark blue box region), a secretion signal peptide (green box region), a mature lactase-phlorizin hydrolase domain (domain III and IV colored by pink box region), and a novel 3'-UTR region (light blue box region). The vector constructed in a plasmid as stated above was amplified by shaking the culture in 500-ml volume of bacterial host cells and purified by plasmid DNA extraction in lysozyme and alkali reagent. A transgene construct of high purity was obtained following a preparation process comprising double digestions of HindIII and XbaI restriction enzymes and CsCl-gradient ultracentrifugation for DNA banding processing. The transgene was mixed at a concentration of 1-2 ng/μl into a suitable microinjection buffer (10 mM Tris-HCl, 0.1 mM EDTA; pH 7.4), and injected into a male pronucleous of mammal one-cell stage embryos by the microinjection technique. The embryos were then transferred into the uterus of a female mammal. For the animal subjects born after pregnancy, rapid PCR screening and Southern blotting were performed on their tissue DNA to analyze the insertion pattern of the heterologous transgene in the animal genome. The results are shown in FIGS. 3B to 3D. One strain of transgenic dairy goats and 7 strains of transgenic mice were obtained by this method.

The nucleotide sequencing analysis showed that there was only one BamHI restriction site located near the 3'-end of the ecLPH transgene (FIG. 3A). Therefore, the insertion and possible concatamerizing patterns of the LPH transgene in the chromosomes of each mouse were determined by Southern blot hybridization. Based on the resulting signals, it was determined that the heterologous gene was inserted in the mouse genome with various concatamerizing patterns. The concatamerizing patterns of the heterologous gene included head-to-head, tail-to-tail and head-to-tail concatamerization. Moreover, the heterologous genes in parental transgenic mice No. 1 and No. 3 were passed to their offspring without difference in the concatamerizing pattern (FIG. 3B). As for parental transgenic mouse No. 5, the heterologous gene existed in the genome of its offspring mostly in a concatamerizing pattern wherein 5.5 kb was missing, except that No. 102 received the complete heterologous gene (FIG. 3C). These results showed that the heterologous genes in all of the three strains could be completely passed through the germline transmission.

EXAMPLE 3

Quantitative Analysis of Milk of the Transgenic Female Mice

Milk samples of the transgenic female mice of Example 2 were collected for quantitative analysis. A glass pipette sealed by mineral oil was used to collect milk samples. Milk was drawn from anesthetized transgenic female mice, which were treated with oxytocin, by squeezing massage. Milk samples were collected on the $7^{th}$ and $14^{th}$ days. The milk of No. 1 ($F_0$; female) and No. 3 ($F_0$; female) of the parental generation, and that of No. 136 and No. 137 of the filial generation (offspring of No. 5 ($F_0$; male)) were sampled during their lactation. Since mouse milk contains large amounts of casein and lipid, the collected milk samples were first diluted 20-fold with deionized water, and then centrifuged at 3,000 rpm for 10 minutes at 4° C. The whey portion was taken so that the lipid would not interfere with the gel electrophoresis of proteins. The partially purified milk was subjected to polyacrylamide gel electrophoresis (12% SDS-PAGE) for 1.5 hours running time under 100 volts and stained with Coomassie blue. The proteins on the electrophoresis gel were transferred to a PVDF cellulose membrane to perform Western blotting. A rabbit anti-LPH antibody was used to examine the amount of ecLPH proteins in the skim milk of transgenic mice by Western blot hybridization and ELISA assays. The result showed that a specific signal appeared at a molecular weight of 66 kD. The signal was not observed in normal ICR mice of the same strain. Therefore, the exogenic human ecLPH protein was indeed expressed in the mammary gland and secreted in the milk of transgenic animals (FIG. 4). Using β-casein as an internal control to obtain a quantitative calibrated value, it was determined that the amount of the exogenic human ecLPH protein in the milk of transgenic mice at the $14^{th}$ day of the lactating period was much higher than that in the milk of the $7^{th}$ day. The highest amount of the exogenic human ecLPH protein detected from the milk of the transgenic animals was 780 μg/ml. It was clearly demonstrated that the newly cloned ecLPH gene encoded an extracellular secreting ecLPH protein.

EXAMPLE 4

Immuno-histochemistry Staining Analysis of Mammary-gland Tissue Sections of the Transgenic Female Mice To examine the difference in the expression level of the exogenic human ecLPH protein between homozygous $F_3$ offspring subjects (ecLPH+/+) and heterozygous $F_3$ offspring subjects (ecLPH+/−), the transgenic female mice produced according to the method of Example 2 were sacrificed during their lactation period, and their mammary gland tissues were taken for freeze embedding sectioning and immuno-histochemistry staining (IHC). It was clearly observed from the staining that there were red signals resulting from AEC chromogens (peroxidase substrate) degraded by HRP (horseradish peroxidase) enzymes bound on the secondary antibodies, representing target proteins in the mammary glands of the transgenic mice, which were recognized by the specific monoclonal antibodies. Treated by the same IHC conditions, no equivalent signal was observed in the mice of the normal ICR control group ( FIGS. 5A to 5C). Therefore, it was determined that the target protein was indeed expressed in the mammary glands of the transgenic mice, and that homozygous transgenic female mice had higher expression than heterozygous ones. As for the location of expression in mammary-gland tissues, signals clearly appeared in the epithelia, alvoli cavities and lactiferous tubules. This result directly indicated that the exogenic human ecLPH protein pertains to the extracellular form.

EXAMPLE 5

X-Fuc Activity Staining Analysis of Mammary Gland Tissue Sections of the ecLPH Transgenic Female Mice To further examine the physiological enzyme activity of the ecLPH proteins in the milk of the transgenic animals, both transgenic female mice and normal ICR female mice were sacrificed on the $14^{th}$ day of their lactation period, and their mammary-gland tissues were taken for freeze embedding sectioning and activity staining with an LPH-specific X-Fuc chromogen substrate. The chromogen substrate is an analog of 5-bromo-4-chloro-3-indolyl β-D-galactoside (X-gal), differing in that X-Fuc is specifically degraded by the lactase-phlorizin hydrolase domain of LPH enzyme to produce a signal of a blue degraded product. The tissues were fixed on slides with 4% paraformaldehyde in room temperature for 30 minutes and washed 3 times with phosphate buffered saline (PBS). The slides with cells attached and fixed thereon were covered with 1 mM X-Fuc (the lactase-specific chromogen substrate) dissolved in 1 M maleate buffer (pH6.5) containing 0.5 mM p-chloromercuribenzoate, 0.05 M potassium ferricyanide and 0.05 M potassium ferrocyanide, and carefully put in a chamber with sufficient moisture. The slides were left overnight at 37° C. for reaction, and excessive fluid resulting from the reaction was removed. The slides were washed twice with PBS, covered with 80% glycerin and sealed. The slides were observed under a microscope for coloration, and photographed with a digital camera for recording. In FIG. 6B, blue signals resulting from degradation of the X-Fuc substrate clearly appeared in the alveoli cavity of the mammary gland of the ecLPH transgenic mice, while no blue signal was generated at the same location of the control group of normal ICR female mice (FIG. 6C). In contrast, we also generated a control transgenic mice harboring the prior art membrane-anchored LPH gene in the same mammary expression vector to compare their protein localization and enzyme activity in the mammary gland. The blue stain of degradation of X-Fuc substrate was only presented near the epithelial layer in the mammary gland of the LPH transgenic mice as shown in FIG. 6A.

EXAMPLE 6

Examination of Lactose-degrading Ability of ecLPH Enzymes in the Milk of the Transgenic Animals It was determined from the results obtained in the previous examples that ecLPH could be highly expressed in the mammary gland, and the activity thereof has been proved with X-Fuc. However, direct evidence proving the degradation ability of ecLPH is still required for confirming if ecLPH can completely decompose the lactose in milk. When lactose is decomposed, two monosaccharide molecules, galactose and glucose, are generated. Therefore, except for directly proving the degradation of lactose, detecting the increase in the amounts of galactose and glucose can also be utilized to confirm if the heterologous hLPH1 resulting from the expression of the ecLPH gene can decompose lactose, the major disaccharide molecule in milk. In the present invention, standard samples of glucose, the monosaccharide molecule and lactose, the disaccharide molecule were established by HPLC analysis for comparison with the test samples (FIG. 7A). In the HPLC separation curve of the milk sample from a normal ICR mouse (FIG. 7B), only the peak of lactose appeared, which was used as the control of normal mouse milk in the present experiment. In the HPLC map of the milk sample from the ecLPH transgenic mouse (FIG. 7C), the peaks of both lactose and glucose clearly appeared. This result showed that 50% of the lactose was degraded into glucose. As for the HPLC map of the milk sample from a non-transgenic mouse (FIG. 7D), only one peak appeared, proving that the milk contains only lactose, the same as that of the normal ICR mouse.

EXAMPLE 7

Comparison of the Growth Curves of ecLPH Transgenic Mice and Normal ICR Mice

Transgenic female mice and normal ICR female mice were bred at the same time. The $4^{th}$ day after the delivery was the first day of measuring the weights of the filial mice. Afterwards, the weight of each of the filial mice was measured every two days. The results of the weights measured on the $4^{th}$ day and thereafter showed that the filial mice receiving milk from these LPH transgenic mice of the present invention (n=26) increased more than the weight of the normal ICR control group (n=19), with a statistically significant difference of $p<0.001$ (shown in FIG. 8). Such results not only showed that the novel ecLPH protein had a function of degrading lactose, but also suggested that the transformed monosaccharide components (i.e., glucose and galactose) could be digested more easily and might provide assistance in intestinal digestion and absorption. The results showed that the ecLPH-containing milk can increase the growth rate and weight gain of newborn animals by predigestion of lactose in their nursing milk.

The present invention successfully cloned the novel extracellular lactase-phlorizin hydrolase (ecLPH) gene, and transformed mammals like dairy goats and mice with the human ecLPH gene. The transgene can be continuously and stably expressed during lactation, producing large amounts of proteins having the activity of degrading lactose. The expression of the heterologous gene in tissues of the mammary gland does not affect the normal physiological functions of the transgenic animal. The transgene specific for mammary gland expression even lacks any additional selection gene for antibiotic resistance. Further, mammals transformed by the technology of the present invention breed filial generations carrying the heterologous transgene, with amounts of expression comparable to their transformed parental generation and thus can be used to produce low-lactose milk.

Without departing from the spirit and scope of the present invention, in view of the present disclosure, anyone skilled in the art may make various changes and modifications to introduce different heterologous genes, which falls within the protected scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An isolated nucleic acid molecule consisting of a nucleotide sequence encoding the amino acid sequence of SEQ ID NO:2.

2. The isolated nucleic acid molecule of claim 1 consisting of the nucleotide sequence of SEQ ID NO:1.

3. A mammary gland-specific expression vector comprising a nucleic acid molecule encoding a mature protein of a human extracellular lactase-phlorizin hydrolase protein consisting of the amino acid sequence of SEQ ID NO:2, wherein the mature protein has no signal peptide sequence, wherein the mammary gland-specific expression vector expresses the mature protein of the human extracellular lactase-phlorizin hydrolase protein in a mammary gland of a transgenic mammal transformed with the mammary gland-specific expression vector.

4. The mammary gland-specific expression vector of claim 3, comprising:
   (a) a first nucleotide sequence encoding a mammary gland-specific extracellular signal peptide sequence;
   (b) a second nucleotide sequence encoding the mature protein of the human extracellular lactase-phlorizin hydrolase protein, linked to the 3'-end of the first nucleotide sequence, wherein the signal peptide sequence guides the secretion of the mature protein into milk produced by the transgenic mammal;
   (c) a third nucleotide sequence encoding a 3'-untranslated region (3'-UTR), linked to the 3'-end of the second nucleotide sequence, wherein the 3'-UTR comprises a polyadenylation signal; and
   (d) a promoter sequence linked to the 5'-end of the first nucleotide sequence, wherein the promoter sequence regulates the transcription of a gene comprising the first nucleotide sequence, the second nucleotide sequence and the third nucleotide sequence, in mammary gland epithelial cells of the transgenic mammal during a lactation period of the transgenic mammal.

5. The mammary gland-specific expression vector of claim 4, wherein the promoter sequence comprises alpha-lactalbumin ($\alpha$-LA) promoter.

6. The mammary gland-specific expression vector of claim 4, wherein the mature protein of the human extracellular lactase-phlorizin hydrolase protein consists of domains III and IV of the human extracellular lactase-phlorizin hydrolase protein.

* * * * *

SEQUENCE LISTING

<160> NUMBER OF SEQ ID NOS: 7

<210> SEQ ID NO 1

<211> LENGTH: 3246
<212> TYPE: DNA
<213> ORGANISM: Homo sapiens

<400> SEQUENCE: 1

| | | | | | |
|---|---|---|---|---|---|
| atgaaacttc | tcatccttac | ctgtcttgtg | gctgttgctg | ccaggttaac | cctcccctcc | 60 |
| aaagtcagag | ccttcacttt | tccatctgag | gtgccctcca | aggctaaagt | cgtttgggaa | 120 |
| aagttctcca | gccaacccaa | gttcgaaaga | gatttgttct | accacgggac | gtttcgggat | 180 |
| gactttctgt | ggggcgtgtc | ctcttccgct | tatcagattg | aaggcgcgtg | ggatgccgat | 240 |
| ggcaaaggcc | ccagcatctg | gataacttt | acccacacac | cagggagcaa | tgtgaaagac | 300 |
| aatgccactg | gagacatcgc | ctgtgacagc | tatcaccagc | tggatgccga | tctgaatatg | 360 |
| ctccgagctt | tgaaggtgaa | ggcctaccgc | ttctctatct | cctggtctcg | gattttccca | 420 |
| actgggagaa | acagctctat | caacagtcat | ggggttgatt | attacaacag | gctgatcaat | 480 |
| ggcttggtgg | caagcaacat | ctttcccatg | gtgacattgt | tccattggga | cctgccccag | 540 |
| gccctccagg | atatcggagg | ctgggagaat | cctgccttga | ttgacttgtt | tgacagctac | 600 |
| gcagactttt | gtttccagac | cttggtgat | agagtcaagt | tttggatgac | ttttaatgag | 660 |
| cccatgtacc | tggcatggct | aggttatggc | tcaggggaat | tcccccagg | ggtgaaggac | 720 |
| ccaggctggg | caccatatag | gatagcccac | gccgtcatca | aagcccatgc | cagagtctat | 780 |
| cacacgtacg | atgagaaata | caggcaggag | cagaaggggg | tcatctcgct | gagcctcagt | 840 |
| acacactggg | cagagcccaa | gtcaccaggg | gtccccagag | atgtggaagc | cgctgaccga | 900 |
| atgctgcagt | tctccctggg | ctggtttgct | caccccattt | ttagaaacgg | agactatcct | 960 |
| gacaccatga | agtggaaagt | ggggaacagg | agtgaactgc | agcacttagc | cacctcccgc | 1020 |
| ctgccaagct | tcactgagga | agagaagagg | ttcatcaggg | cgacggccga | cgtcttctgc | 1080 |
| ctcaacacgt | actactccag | aatcgtgcag | cacaaaacac | ccaggctaaa | cccaccctcc | 1140 |
| tacgaagacg | accaggagat | ggctgaggag | gaggacccctt | cgtggccttc | cacggcaatg | 1200 |
| aacagagctg | cgccctgggg | gacgcgaagg | ctgctgaact | ggatcaagga | agagtatggt | 1260 |
| gacatcccca | tttacatcac | cgaaaacgga | gtggggctga | ccaatccgaa | cacggaggat | 1320 |
| actgatagga | tattttacca | caaaacctac | atcaatgagg | ctttgaaagc | ctacaggctc | 1380 |
| gatggtatag | accttcgagg | gtatgtcgcc | tggtctctga | tggacaactt | tgagtggcta | 1440 |
| aatggctaca | cggtcaagtt | tggactgtac | catgttgatt | tcaacaacac | gaacaggcct | 1500 |
| cgcacagcaa | gagcctccgc | caggtactac | acagaggtca | ttaccaacaa | cggcatgcca | 1560 |
| ctggccaggg | aggatgagtt | tctgtacgga | cggtttcctg | agggcttcat | ctggagtgca | 1620 |
| gcttctgctg | catatcagat | tgaaggtgcg | tggagagcag | atggcaaagg | actcagcatt | 1680 |
| tgggacacgt | ttctcacac | accactgagg | gttgagaacg | atgccattgg | agacgtggcc | 1740 |
| tgtgacagtt | atcacaagat | tgctgaggat | ctggtcaccc | tgcagaacct | gggtgtgtcc | 1800 |
| cactaccgtt | tttccatctc | ctggtctcgc | atcctccctg | atggaaccac | caggtacatc | 1860 |
| aatgaagcgg | gcctgaacta | ctacgtgagg | ctcatcgata | cactgctggc | cgccagcatc | 1920 |
| cagcccagg | tgaccattta | ccactgggac | ctaccacaga | cgctccaaga | tgtaggaggc | 1980 |
| tgggagaatg | agaccatcgt | gcagcggttt | aaggagtatg | cagatgtgct | cttccagagg | 2040 |
| ctgggagaca | aggtgaagtt | ttggatcacg | ttgaatgagc | cctttgtcat | tgcttaccag | 2100 |
| ggctatggct | acggaacagc | agctccagga | gtctccaata | ggcctggcac | tgcccctac | 2160 |
| attgttggcc | acaatctaat | aaaggctcat | gctgaggcct | ggcatctgta | caacgatgtg | 2220 |

-continued

```
taccgcgcca gtcaaggtgg cgtgatttcc atcaccatca gcagtgactg ggctgaaccc      2280
agagatccct ctaaccagga ggatgtggag gcagccagga gatatgttca gttcatggga      2340
ggctggtttg cacatcctat tttcaagaat ggagattaca atgaggtgat gaagacgcgg      2400
atccgtgaca ggagcttggc tgcaggcctc aacaagtctc ggctgccaga atttacagag      2460
agtgagaaga ggaggatcaa cggcacctat gacttttttg ggttcaatca ctacaccact      2520
gtcctcgcct acaacctcaa ctatgccact gccatctctt cttttgatgc agacagagga      2580
gttgcttcca tcgcagatcg ctcgtggcca gactctggct ccttctggct gaagatgacg      2640
ccttttggct tcaggaggat cctgaactgg ttaaaggagg aatacaatga ccctccaatt      2700
tatgtcacag agaatggagt gtcccagcgg gaagaaacag acctcaatga cactgcaagg      2760
atctactacc ttcggactta catcaatgag gccctcaaag ctgtgcagga caaggtggac      2820
cttcgaggat acacagtttg gagtgcgata gacaattttg agtgggccac aggcttttca      2880
gagagatttg gtctgcattt tgtgaactac agtgacccct ctctgccaag gatccccaaa      2940
gcatcagcga agttctacgc ctctgtggtc cgatgcaatg gcttccctga ccccgctaca      3000
gggcctcacg cttgtctcca ccagccagat gccggaccca ccatcagccc cgtgagacag      3060
gaggaggtgc agttcctggg gctaatgctc ggcatcacag aagcacagac agcttttgtac     3120 gttctctttt ctcttgtgct tcttggagtc tgtggcttgg catttctgtc atacaagtac      3180
tgcaagcgct ctaagcaagg gaaaacacaa cgaagccaac aggaattgag cccggtgtct      3240
tcattc                                                                  3246
```

<210> SEQ ID NO 2
<211> LENGTH: 1082
<212> TYPE: PRT
<213> ORGANISM: Homo sapiens

<400> SEQUENCE: 2

```
Met Lys Leu Leu Ile Leu Thr Cys Leu Val Ala Val Ala Ala Arg Leu
1               5                   10                  15

Thr Leu Pro Ser Lys Val Arg Ala Phe Thr Phe Pro Ser Glu Val Pro
            20                  25                  30

Ser Lys Ala Lys Val Val Trp Glu Lys Phe Ser Ser Gln Pro Lys Phe
        35                  40                  45

Glu Arg Asp Leu Phe Tyr His Gly Thr Phe Arg Asp Phe Leu Trp
    50                  55                  60

Gly Val Ser Ser Ser Ala Tyr Gln Ile Glu Gly Ala Trp Asp Ala Asp
65                  70                  75                  80

Gly Lys Gly Pro Ser Ile Trp Asp Asn Phe Thr His Thr Pro Gly Ser
                85                  90                  95

Asn Val Lys Asp Asn Ala Thr Gly Asp Ile Ala Cys Asp Ser Tyr His
            100                 105                 110

Gln Leu Asp Ala Asp Leu Asn Met Leu Arg Ala Leu Lys Val Lys Ala
        115                 120                 125

Tyr Arg Phe Ser Ile Ser Trp Ser Arg Ile Phe Pro Thr Gly Arg Asn
    130                 135                 140

Ser Ser Ile Asn Ser His Gly Val Asp Tyr Tyr Asn Arg Leu Ile Asn
145                 150                 155                 160

Gly Leu Val Ala Ser Asn Ile Phe Pro Met Val Thr Leu Phe His Trp
                165                 170                 175

Asp Leu Pro Gln Ala Leu Gln Asp Ile Gly Gly Trp Glu Asn Pro Ala
```

-continued

```
                180                 185                 190
Leu Ile Asp Leu Phe Asp Ser Tyr Ala Asp Phe Cys Phe Gln Thr Phe
            195                 200                 205
Gly Asp Arg Val Lys Phe Trp Met Thr Phe Asn Glu Pro Met Tyr Leu
            210                 215                 220
Ala Trp Leu Gly Tyr Gly Ser Gly Glu Phe Pro Pro Gly Val Lys Asp
225                 230                 235                 240
Pro Gly Trp Ala Pro Tyr Arg Ile Ala His Ala Val Ile Lys Ala His
                245                 250                 255
Ala Arg Val Tyr His Thr Tyr Asp Glu Lys Tyr Arg Gln Glu Gln Lys
            260                 265                 270
Gly Val Ile Ser Leu Ser Leu Ser Thr His Trp Ala Glu Pro Lys Ser
            275                 280                 285
Pro Gly Val Pro Arg Asp Val Glu Ala Ala Asp Arg Met Leu Gln Phe
            290                 295                 300
Ser Leu Gly Trp Phe Ala His Pro Ile Phe Arg Asn Gly Asp Tyr Pro
305                 310                 315                 320
Asp Thr Met Lys Trp Lys Val Gly Asn Arg Ser Glu Leu Gln His Leu
                325                 330                 335
Ala Thr Ser Arg Leu Pro Ser Phe Thr Glu Glu Lys Arg Phe Ile
            340                 345                 350
Arg Ala Thr Ala Asp Val Phe Cys Leu Asn Thr Tyr Tyr Ser Arg Ile
            355                 360                 365
Val Gln His Lys Thr Pro Arg Leu Asn Pro Pro Ser Tyr Glu Asp Asp
            370                 375                 380
Gln Glu Met Ala Glu Glu Asp Pro Ser Trp Pro Ser Thr Ala Met
385                 390                 395                 400
Asn Arg Ala Ala Pro Trp Gly Thr Arg Arg Leu Leu Asn Trp Ile Lys
                405                 410                 415
Glu Glu Tyr Gly Asp Ile Pro Ile Tyr Ile Thr Glu Asn Gly Val Gly
                420                 425                 430
Leu Thr Asn Pro Asn Thr Glu Asp Thr Asp Arg Ile Phe Tyr His Lys
            435                 440                 445
Thr Tyr Ile Asn Glu Ala Leu Lys Ala Tyr Arg Leu Asp Gly Ile Asp
            450                 455                 460
Leu Arg Gly Tyr Val Ala Trp Ser Leu Met Asp Asn Phe Glu Trp Leu
465                 470                 475                 480
Asn Gly Tyr Thr Val Lys Phe Gly Leu Tyr His Val Asp Phe Asn Asn
                485                 490                 495
Thr Asn Arg Pro Arg Thr Ala Arg Ala Ser Ala Arg Tyr Tyr Thr Glu
                500                 505                 510
Val Ile Thr Asn Asn Gly Met Pro Leu Ala Arg Glu Asp Glu Phe Leu
            515                 520                 525
Tyr Gly Arg Phe Pro Glu Gly Phe Ile Trp Ser Ala Ser Ala Ala
            530                 535                 540
Tyr Gln Ile Glu Gly Ala Trp Arg Ala Asp Gly Lys Gly Leu Ser Ile
545                 550                 555                 560
Trp Asp Thr Phe Ser His Thr Pro Leu Arg Val Glu Asn Asp Ala Ile
                565                 570                 575
Gly Asp Val Ala Cys Asp Ser Tyr His Lys Ile Ala Glu Asp Leu Val
            580                 585                 590
Thr Leu Gln Asn Leu Gly Val Ser His Tyr Arg Phe Ser Ile Ser Trp
            595                 600                 605
```

-continued

```
Ser Arg Ile Leu Pro Asp Gly Thr Thr Arg Tyr Ile Asn Glu Ala Gly
    610                 615                 620

Leu Asn Tyr Tyr Val Arg Leu Ile Asp Thr Leu Leu Ala Ala Ser Ile
625                 630                 635                 640

Gln Pro Gln Val Thr Ile Tyr His Trp Asp Leu Pro Gln Thr Leu Gln
                    645                 650                 655

Asp Val Gly Gly Trp Glu Asn Glu Thr Ile Val Gln Arg Phe Lys Glu
                660                 665                 670

Tyr Ala Asp Val Leu Phe Gln Arg Leu Gly Asp Lys Val Lys Phe Trp
            675                 680                 685

Ile Thr Leu Asn Glu Pro Phe Val Ile Ala Tyr Gln Gly Tyr Gly Tyr
    690                 695                 700

Gly Thr Ala Ala Pro Gly Val Ser Asn Arg Pro Gly Thr Ala Pro Tyr
705                 710                 715                 720

Ile Val Gly His Asn Leu Ile Lys Ala His Ala Glu Ala Trp His Leu
                    725                 730                 735

Tyr Asn Asp Val Tyr Arg Ala Ser Gln Gly Gly Val Ile Ser Ile Thr
                740                 745                 750

Ile Ser Ser Asp Trp Ala Glu Pro Arg Asp Pro Ser Asn Gln Glu Asp
            755                 760                 765

Val Glu Ala Ala Arg Arg Tyr Val Gln Phe Met Gly Gly Trp Phe Ala
    770                 775                 780

His Pro Ile Phe Lys Asn Gly Asp Tyr Asn Glu Val Met Lys Thr Arg
785                 790                 795                 800

Ile Arg Asp Arg Ser Leu Ala Ala Gly Leu Asn Lys Ser Arg Leu Pro
                    805                 810                 815

Glu Phe Thr Glu Ser Glu Lys Arg Arg Ile Asn Gly Thr Tyr Asp Phe
                820                 825                 830

Phe Gly Phe Asn His Tyr Thr Thr Val Leu Ala Tyr Asn Leu Asn Tyr
            835                 840                 845

Ala Thr Ala Ile Ser Ser Phe Asp Ala Asp Arg Gly Val Ala Ser Ile
850                 855                 860

Ala Asp Arg Ser Trp Pro Asp Ser Gly Ser Phe Trp Leu Lys Met Thr
865                 870                 875                 880

Pro Phe Gly Phe Arg Arg Ile Leu Asn Trp Leu Lys Glu Glu Tyr Asn
                    885                 890                 895

Asp Pro Pro Ile Tyr Val Thr Glu Asn Gly Val Ser Gln Arg Glu Glu
                900                 905                 910

Thr Asp Leu Asn Asp Thr Ala Arg Ile Tyr Tyr Leu Arg Thr Tyr Ile
            915                 920                 925

Asn Glu Ala Leu Lys Ala Val Gln Asp Lys Val Asp Leu Arg Gly Tyr
    930                 935                 940

Thr Val Trp Ser Ala Ile Asp Asn Phe Glu Trp Ala Thr Gly Phe Ser
945                 950                 955                 960

Glu Arg Phe Gly Leu His Phe Val Asn Tyr Ser Asp Pro Ser Leu Pro
                    965                 970                 975

Arg Ile Pro Lys Ala Ser Ala Lys Phe Tyr Ala Ser Val Val Arg Cys
                980                 985                 990

Asn Gly Phe Pro Asp Pro Ala Thr Gly Pro His Ala Cys Leu His Gln
            995                 1000                1005

Pro Asp Ala Gly Pro Thr Ile Ser Pro Val Arg Gln Glu Glu Val
    1010                1015                1020
```

```
Gln Phe Leu Gly Leu Met Leu Gly Ile Thr Glu Ala Gln Thr Ala
    1025                1030                1035

Leu Tyr Val Leu Phe Ser Leu Val Leu Leu Gly Val Cys Gly Leu
    1040                1045                1050

Ala Phe Leu Ser Tyr Lys Tyr Cys Lys Arg Ser Lys Gln Gly Lys
    1055                1060                1065

Thr Gln Arg Ser Gln Gln Glu Leu Ser Pro Val Ser Ser Phe
    1070                1075                1080

<210> SEQ ID NO 3
<211> LENGTH: 20
<212> TYPE: DNA
<213> ORGANISM: Artificial
<220> FEATURE:
<223> OTHER INFORMATION: Primer 1

<400> SEQUENCE: 3
ctctcttgtc atcctcttcc                                                 20

<210> SEQ ID NO 4
<211> LENGTH: 20
<212> TYPE: DNA
<213> ORGANISM: Artificial
<220> FEATURE:
<223> OTHER INFORMATION: Primer 2

<400> SEQUENCE: 4
aacaagtcaa tcaaggcagg                                                 20

<210> SEQ ID NO 5
<211> LENGTH: 20
<212> TYPE: DNA
<213> ORGANISM: Artificial
<220> FEATURE:
<223> OTHER INFORMATION: Primer 3

<400> SEQUENCE: 5
cagacttttg tttccagacc                                                 20

<210> SEQ ID NO 6
<211> LENGTH: 18
<212> TYPE: DNA
<213> ORGANISM: Artificial
<220> FEATURE:
<223> OTHER INFORMATION: Primer 4

<400> SEQUENCE: 6
tcaacaacac gaacaggc                                                   18

<210> SEQ ID NO 7
<211> LENGTH: 20
<212> TYPE: DNA
<213> ORGANISM: Artificial
<220> FEATURE:
<223> OTHER INFORMATION: Primer 5

<400> SEQUENCE: 7
acagaaatgc caagccacag                                                 20
```